US010736982B2

(12) United States Patent
Xia et al.

(10) Patent No.: US 10,736,982 B2
(45) Date of Patent: Aug. 11, 2020

(54) WATER-BASED STERILIZATION INDICATOR COMPOSITION

(71) Applicant: 3M INNOVATIVE PROPERTIES COMPANY, Saint Paul, MN (US)

(72) Inventors: Wensheng Xia, Woodbury, MN (US); Sarah J. Davis, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 198 days.

(21) Appl. No.: 16/066,933

(22) PCT Filed: Jan. 13, 2017

(86) PCT No.: PCT/US2017/013391
§ 371 (c)(1),
(2) Date: Jun. 28, 2018

(87) PCT Pub. No.: WO2017/127297
PCT Pub. Date: Jul. 27, 2017

(65) Prior Publication Data
US 2019/0008990 A1  Jan. 10, 2019

Related U.S. Application Data

(60) Provisional application No. 62/279,991, filed on Jan. 18, 2016.

(51) Int. Cl.
*G01N 31/22* (2006.01)
*A61L 2/28* (2006.01)
*A61L 2/07* (2006.01)
*C09D 11/50* (2014.01)
*C09D 11/037* (2014.01)
*C09D 11/107* (2014.01)

(52) U.S. Cl.
CPC ...... *A61L 2/28* (2013.01); *A61L 2/07* (2013.01); *C09D 11/037* (2013.01); *C09D 11/107* (2013.01); *C09D 11/50* (2013.01); *G01N 31/226* (2013.01)

(58) Field of Classification Search
CPC .. G01N 31/22; A61L 2/28; A61L 2/07; C09D 11/037; C09D 11/107; C09D 11/50
USPC ............................................................ 436/1
See application file for complete search history.

(56) References Cited

U.S. PATENT DOCUMENTS

| 2,118,144 | A | * | 5/1938 | Chaney | G01K 11/12 374/162 |
| 3,360,338 | A | * | 12/1967 | Edenbaum | C09D 11/50 422/429 |
| 3,386,807 | A | * | 6/1968 | Edenbaum | A61L 2/28 422/425 |
| 3,471,422 | A | * | 10/1969 | Edlein | C08K 5/0041 436/1 |
| 3,616,898 | A | * | 11/1971 | Massie | B65D 75/30 206/216 |
| 4,181,500 | A | * | 1/1980 | Cowsar | G01N 33/525 436/99 |
| 5,057,433 | A | * | 10/1991 | Douglas | A61L 2/28 422/119 |
| 5,217,691 | A |   | 6/1993 | Greene |  |
| 5,916,816 | A |   | 6/1999 | Read |  |
| 9,170,245 | B2 | * | 10/2015 | Landgrebe | A61L 2/28 |
| 9,176,103 | B2 |   | 11/2015 | Whitman |  |
| 9,588,052 | B2 | * | 3/2017 | Landgrebe | C09D 11/50 |
| 9,951,370 | B2 | * | 4/2018 | Yu | G01N 31/226 |
| 2011/0275159 | A1 | * | 11/2011 | Landgrebe | A61L 2/28 436/1 |
| 2011/0312096 | A1 |   | 12/2011 | Whitman |  |
| 2014/0370604 | A1 |   | 12/2014 | Landgrebe |  |
| 2015/0328352 | A1 | * | 11/2015 | Yu | A61L 2/28 436/1 |

FOREIGN PATENT DOCUMENTS

| JP | 2-211162 | * | 8/1990 |
| JP | H04-062746 |   | 10/1992 |
| JP | H04-364174 |   | 12/1992 |
| WO | WO 2014-106020 |   | 7/2014 |

OTHER PUBLICATIONS

International Search Report for PCT International Application No. PCT/US2017/013391, dated Apr. 3, 2017, 3 pages.

* cited by examiner

*Primary Examiner* — Arlen Soderquist
(74) *Attorney, Agent, or Firm* — 3M Innovative Properties Company; Trisha D. Adamson

(57) ABSTRACT

Water-based formulations comprising an indicating composition dispersed in water are described. The water-based indicating compositions include an organic Bi(III) compound, a sulfur source, a carbonate salt, and strontium hydroxide. Formulations further including a resin and/or an acidic additive are also described.

14 Claims, No Drawings

WATER-BASED STERILIZATION INDICATOR COMPOSITION

CROSS REFERENCE TO RELATED APPLICATIONS

This application is a national stage filing under 35 U.S.C. 371 of International Application No. PCT/US2017/013391, filed Jan. 13, 2017, which claims the benefit of Provisional Application No. 62/279,991, filed Jan. 18, 2016. The disclosures of both applications are incorporated by reference in their entirety herein.

FIELD

The present disclosure relates to water-based compositions containing organic Bi(III) compounds, carbonate salts, a sulfur source, and strontium hydroxide. The use of such compositions to form steam sterilization indicators is also described.

SUMMARY

Briefly, in one aspect, the present disclosure provides an indicator formulation comprising an indicating composition dispersed in water. The indicating composition comprises an organic Bi(III) compound; a sulfur source; a carbonate salt, and strontium hydroxide. The organic Bi(III) compound and the sulfur source are selected such that at least one of the organic Bi(III) compound and the sulfur source has solubility in water at 20° C. of less than 5 grams/100 ml. In some embodiments, both the organic Bi(III) compound and the sulfur source have solubility in water at 20° C. of less than 5 grams/100 ml. The strontium hydroxide provides resistance to hydrogen peroxide bleaching after steam sterilization cycles and a reduction in ink transfer.

In some embodiments, the composition comprises bismuth subcarbonate formed in situ. In some embodiments, the organic Bi(III) is selected from the group consisting of bismuth subsalicylate, bismuth citrate, bismuth tartrate, and combinations thereof. In some embodiments, the sulfur source is selected from the group consisting of sulfur, 1,3-diphenylthiourea, sodium thiosulfate, and combinations thereof. In some embodiments, the carbonate salt is selected from the group consisting of lithium carbonate, magnesium carbonate, sodium carbonate, sodium bicarbonate, and combinations thereof.

In some embodiments, the formulation further comprises an acidic compound, e.g., citric acid, gallic acid, oxalic acid, and combinations thereof.

In some embodiments, the formulation further comprises a resin, e.g., an acrylic resin.

In another aspect, the present disclosure provides an indicator tape comprising a substrate and an indicator composition on a portion of at least one surface of the substrate. The indicator tape is prepared by the process of applying an indicator formulation of the present disclosure to the surface of the substrate and drying the formulation.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

A variety of products and articles, including, for example, medical instruments, devices, and equipment, must be sterilized prior to use to prevent bio-contamination of a wound site, a sample, an organism, or the like. A number of sterilization processes are used that involve contacting the product or article with a sterilant. Examples of such sterilants include steam, ethylene oxide, hydrogen peroxide, and the like. Steam sterilization is widely used, at least in part because multiple batches of articles can be subjected to sterilization conditions during a 24 hour period using a single steam sterilizer.

Monitoring for conditions sufficient for steam sterilization is generally carried out by placing an appropriate sterilization indicator along with the product and/or article to be sterilized within a sterilization chamber. A variety of sterilization indicators, including chemical and biological indicators, are known and used for this purpose. Chemical indicators offer an advantage in that they can be read immediately at the end of a sterilization process. For example, internal chemical indicators are placed within an instrument tray prior to steam exposure. These indicators are read in the operating room upon opening the steam-exposed tray, prior to instrument removal. Process indicators such as labels and autoclave tapes have been used to indicate that a wrapped instrument tray or other wrapped article or articles have been exposed to steam.

Internal chemical indicators and process indicators, such as autoclave tapes, should indicate by color change their exposure to steam under various operating conditions associated with a level of exposure to steam adequate to achieve sterilization. However, these indicators should remain their original color, or near their original color, under other conditions in which the exposure to steam is inadequate for sterilization. For example, an autoclave tape should show a significant color change when subjected to steam in a hospital autoclave at 132-134° C. for around 3 or 4 minutes, and at 121° C. for around 20 minutes. Additionally, when tested using a steam resistometer according to ISO Standard 11140, an autoclave tape should show a significant color change on contact with steam at 134° C. for 2 minutes, and at 121° C. for 10 minutes, but should not show a significant color change on exposure to steam at 134° C. for 30 seconds nor at 121° C. for 3 minutes. An autoclave tape should not show a significant color change on exposure to dry heat at 140° C. for 30 minutes. Additionally, subsequent to steam exposure, an autoclave tape or other substrate printed with the ink of the present disclosure, preferably will not fade when exposed to hydrogen peroxide vapors and will not transfer ink to surfaces with which it comes into contact.

Steam sterilization indicator compositions for both internal indicators and process indicators that have been used include a polyvalent metal compound such as lead carbonate, and sulfur. Such indicators turn to brown or black when their color is fully developed by a steam sterilization condition. Because of environmental concerns, lead compounds have been and continue to be replaced by other polyvalent metal compounds. For example, U.S. Pat. No. 3,471,422 (Edbohm et al.) describes a time-temperature responsive color changing indicator composition based on a compound of a polyvalent metal and a sulfur material. The polyvalent metal is lead, copper, cobalt, nickel, bismuth, or cadmium. Also, Japanese Patent Kokai No. 4[1992]-364,174 (Takemura et al.) and Japanese Patent Kokai No. 4[1992]-62,746 (Koybayashi et al.) describe bismuth compounds that can be combined with sulfur or sulfur compounds such as thioureas to produce indicator compositions for steam sterilization. However, such compositions do not reliably turn black or even dark brown, and/or they take too long to turn black or dark brown under sterilization conditions of high temperature and humidity, or when exposed to dry heat they undergo a color change that is not markedly different from the color formed when the same composition is exposed to steam.

U.S. Pat. No. 5,916,816 (Read) describes solvent-based steam sterilization indicator compositions using bismuth oxychloride or bismuth subcarbonate, a sulfur source, and a compound capable of generating alkaline conditions when exposed to steam (e.g., carbonate salts). U.S. Pat. No. 9,176,103 ("Chemical Indicator Compositions, Indicators and Methods") also describes solvent-based steam sterilization indicator compositions comprising a bismuth oxide or an organic bismuth compound, a sulfur source, and a compound which makes the composition alkaline when exposed to water vapor at an elevated temperature (e.g., a carbonate salt).

U.S. Patent Publication 2014/0370604 (Landgrebe) describes a water-based composition suitable for forming lead-free chemical indicators that can indicate that a steam sterilization process condition has been met.

Despite these advances, there is a continuing need for a water-based lead-free chemical indicators that can indicate that a steam sterilization process condition has been met and which will, subsequent to steam exposure, will not fade when exposed to hydrogen peroxide vapors and will not transfer ink to surfaces with which it comes into contact Generally, lead-free chemical indicators are useful as steam-sterilization indicators, including autoclave tapes. Generally, acceptable chemical indicators will provide a distinct color change upon exposure to steam at conditions associated with acceptable sterilization conditions, with a distinctly less color change when exposed to dry heat and/or steam at conditions associated with incomplete sterilization. Generally, steam sterilization is associated with conditions wherein steam condenses. As acceptable chemical indicator compositions are designed to turn color upon exposure to the steam and/or condensing water, it was believed that the chemical indicator formulations could not be prepared from water-based solutions; as such solutions would be expected to turn color during their preparation in water. The invention of U.S. Patent Publication 2014/0370604 achieved this objective. The present invention provides a further improvement in that it increases the fully exposed tape's ability to resist fading by hydrogen peroxide vapors when placed adjacent to items activated by, or exposed to hydrogen peroxide. The present invention also provides a further improvement in that it reduces or eliminates the likelihood that the exposed tapes will transfer ink to adjacent surfaces with which they came into contact. Surprisingly, the present inventors discovered that water-based chemical indicator compositions comprising strontium hydroxide could be prepared and used to produce effective steam-sterilization indicators which resist fading when exposed to hydrogen peroxide vapors and resist transferring ink to adjacent surfaces.

Generally, the indicator formulations of the present disclosure include an indicating composition dispersed in water. The indicating composition comprises an organic Bi(III) compound; a sulfur source; a carbonate salt; and strontium hydroxide. At least one of the organic Bi(III) compound and the sulfur source has solubility in water at 20° C. of less than 5 grams/100 ml.

Suitable organic Bi(III) compounds for use in compositions of the present disclosure include bismuth subsalicylate (CAS Reg. No. 14882-18-9), bismuth gallate (3,4,5-trihydroxybenzoic acid bismuth salt, CAS Reg. No. 57206-57-2), bismuth subgallate (2,7-dihydroxy-1,3,2-benzodioxabismol-5-carboxylic acid, CAS Reg. No. 99-26-3), bismuth pyrogallate (1,2,3-benzenetriol, bismuth salt, basic, CAS Reg. No. 12001-49-9), bismuth acetate (bismuth triacetate, CAS Reg. No. 22306-37-2), bismuth citrate (CAS Reg. No. 110230-89-2), bismuth potassium citrate (CAS Reg. No. 57644-54-9), ammonium bismuth citrate (CAS Reg. No. 67953-07-5), bismuth lactate (CAS Reg. No. 6591-53-3), bismuth oxalate (CAS Reg. No. 6591-55-5), bismuth benzoate, bismuth formate, bismuth propionate, bismuth butyrate, bismuth pivalate (bismuth salt of 2,2-dimethylpropanoic acid), 2-propylpentanoic acid bismuth salt (CAS Reg. No. 94071-09-7), bismuth ascorbate, bismuth diethyldithiocarbamate (tris(diethyldithiocarbamato) bismuth (III), CAS Reg. No. 20673-31-8), bismuth dimethyldithiocarbamate, bismuth 2-ethylhexanoate (CAS Reg. No. 67874-71-9), bismuth neodecanoate (CAS Reg. No. 34364-26-6), bismuth oleate, bismuth gluconate, bismuth potassium D-gluconate, bismuth naphtholate (CAS Reg. No. 8039-60-9), naphthenic acid bismuth salt (CAS Reg. No. 85736-59-0), bismuth triglycollamate, bismuth sodium triglycollamate (N,N-bis (carboxymethyl)glycine disodium salt/N-(carboxymethyl)-N-[2-oxo-2-{(oxobismuthino)oxy}ethyl]glycine monosodium salt (3:1), CAS Reg. No. 5798-43-6), bismuth succinate (CAS Reg. No. 139-16-2), bismuth maleate (CAS Reg. No. 88210-84-8), bismuth tartrate (CAS Reg. No. 6591-56-6), bismuth sodium tartrate (CAS Reg. No. 31586-77-3), bismuth potassium tartrate (CAS Reg. No. 5798-41-4), bismuth tannate, 3-camphocarboxylic acid bismuth salt (CAS Reg. No. 4154-53-4), bismuth ethylcamphorate (CAS Reg. No. 52951-37-8), bismuth oxyquinoline (CAS Reg. No. 1300-75-0), 2-oxo-3-bornanecarboxylic acid bismuth salt (CAS Reg. No. 19495-28-4), bismuth valproate, and a combination thereof. Any of the compounds having at least one chiral center includes any one of the stereoisomers or any combination thereof, including racemic mixtures. For example, bismuth gluconate includes all forms of the gluconate (e.g., D-gluconic acid bismuth (III) salt (CAS Reg. No. 94232-39-0), L-gluconic acid bismuth (III) salt, and/or a racemic mixture thereof. For certain of these embodiments, the bismuth (III) compound is selected from the group consisting of bismuth subsalicylate, bismuth citrate, bismuth tartrate, and combinations thereof. For certain of these embodiments, the bismuth (III) compound is bismuth subsalicylate.

Suitable carbonate salts for use in compositions of the present disclosure include potassium carbonate, magnesium carbonate, and sodium carbonate. In some embodiments, bicarbonate salts, including sodium bicarbonate, may be suitable.

The combination of an organic Bi(III) compound with a carbonate salt in water can result in the in situ formation of bismuth subcarbonate. Although the direct addition of bismuth subcarbonate to water failed to form an acceptable chemical indicator, the in situ formation of bismuth subcarbonate from the reaction of an organic Bi(III) compound and a carbonate salt led to good indicating compositions.

A wide variety of sulfur sources may be used in the water-based formulations of the present disclosure. Suitable sulfur sources include elemental sulfur, which is known to exist as an eight-membered ring of sulfur atoms. Under certain alkaline conditions, for example, in the presence of a nucleophile, such as hydroxide ion, the ring of sulfur atoms can be opened and sulfide ions can be formed from the resulting chain of sulfur atoms. In the presence of the sulfide ions, the bismuth compound can form bismuth sulfide, which is dark in color.

Other exemplary sulfur sources include disulfides; thioureas, such as N,N-diphenylthiourea; and thiocarbamates, as well as dithiocarbamates. Additionally, sulfide salts, such as zinc sulfide, calcium sulfide, potassium sulfide can be used as the sulfur source for certain embodiments.

Although a variety of both organic Bi(III) compounds and sulfur sources may be used, these materials should be selected such that at least one of the organic Bi(III) compound or the sulfur source be relatively insoluble in water. For example, at least one of the organic Bi(III) compound or the sulfur source should have solubility in water at 20° C. of less than 5 g/100 ml, e.g., less than 2 g/100 ml, less than 1 g/100 ml, or even less than 0.5 g/100 ml. Generally, the solubility can be determined through any of a variety of known procedures, and the solubility of many compounds is readily available in a variety of commonly available reference materials. As used herein, materials identified in a reference source as "insoluble" or "slightly soluble" are considered to have a solubility of less than 0.5 g/100 ml consistent with the meaning of such phrases to one of ordinary skill in the art.

In some embodiments, the compositions further comprise a resin, also referred to as a binder. Generally, the binder holds the composition in place when coated on a substrate. Preferably the binder comprises a film-forming material, which is stable to heat and water vapor. A film formed by the binder is sufficiently permeable to water vapor and steam to allow a desired color change to occur under sterilization conditions. Materials that the binder may comprise include, for example, styrene, acrylonitrile, acrylate and methacrylate polymers and copolymers (e.g., poly(methylmethacrylate) and methyl/n-butyl methacrylate copolymer), poly(vinyl acetate) and poly(vinylchloride) and copolymers thereof, and various derivatives of cellulose, including, for example, ethylcellulose and nitrocellulose. In certain embodiments, the binder may be an ultraviolet light-, visible light-, or thermally-curable material.

In some embodiments, the compositions of the present disclosure may be used to form an indicator tape. Such tapes may be prepared by coating and/or printing the water-based indicator composition on a substrate and drying the composition. If present, the binder may also be cured and/or crosslinked by, e.g., exposure to actinic radiation and/or heat. Suitable substrates are well-known and include paper, e.g., saturated paper. Generally, any of a variety of known coating and printing techniques may be used.

EXAMPLES

Materials used in the preparation of the following examples are summarized in Table 1.

TABLE 1

| Description | Source |
| --- | --- |
| Strontium hydroxide octahydrate | Sigma, St Louis, MO |
| Dispex Ultra FA 4431 (Dispersing agent) | BASF |
| ACRONAL NX 4569 | BASF |
| Bismuth Subsalicylate | Dudley Corporation |
| Sulfur | Akrochem |
| Lithium carbonate | GFS Chemical |
| Sodium carbonate | J. T. Baker |
| HYCAR 26348 | Lubrizol, WICKLIFFE, OHIO |
| HITAC RA-11 | HITAC ADHESIVES AND COATINGS, Venice, CA |

Comparative Example 1 (CE-1), Example 1 (EX-1), Example 2 (EX-2), and Example 3 (EX-3) were milled using a Hockmeyer Micromill with 1 mm size of zirconia beads. All components were weighed and mixed in a 1000 mL beaker while stirring. The paste was then transferred to the milling chamber to mill for 1 hour at 2,300 rpm. The resulting ink was then transferred to a 1000 mL of bottle. Handspread samples were prepared using #16 Meyer bar on a saturant treated crepe paper. The paper was a saturated 55 gram per square meter basis weight crepe paper with an acrylic top-coat, used to make 3M™ Masking Tape 2060. Samples were then dried at 50° C. for 2 minutes in a baking oven. The ink coated paper was then coated with a layer of acrylic polymer emulsion (25% solids HITAC/HYCAR solution) with #10 bar. The coated samples were dried again for 40 seconds at 150° C.

TABLE 2

EXAMPLE FORMULATIONS

| Components | CE-1 Wt. % | EX-1 Wt. % | EX-2 Wt. % | EX-3 Wt. % |
| --- | --- | --- | --- | --- |
| De-ionized water | 36.04 | 34.64 | 29.56 | 34.14 |
| ACRONAL NX 4569 | 33.92 | 33.92 | 44.00 | 33.92 |
| Lithium carbonate | 1.54 | 1.54 | 1.54 | 1.54 |
| Bismuth subsalicylate | 6.15 | 6.15 | 6.15 | 6.15 |
| Sulfur | 20.00 | 20.00 | 15.00 | 20.00 |
| Strontium hydroxide octahydrate | — | 2.50 | 2.50 | 3.00 |
| Dispersing Agent | — | 1.25 | 1.25 | 1.25 |
| Sodium carbonate | 2.35 | — | — | — |
| Total | 100 | 100 | 100 | 100 |

Hydrogen Peroxide Exposure Test

Examples CE-1, EX-1, EX-2, and EX-3 were cut into 1 inch (2.5 cm) strips and taped on a rectangular KimGuard Sterilization Wrap (KC600, Kimberly-Clark) and then sterilized in an AMSCO LAB 110 using 4 minutes cycles at 132.2° C. The optical densities of the developed samples were recorded using an X-RITE 530 SpectroDensitometer to assess the baseline optical density of the samples before exposure to residual contaminant hydrogen peroxide.

To prepare a hydrogen peroxide exposure fading test scenario, a commonly used hospital plastic tray was loaded with a sterilization load including different surgical tools and a perforated silicon mat inside of the tray. The tray was wrapped with a KIMBERLY-CLARK KC200 KIMGUARD Sterilization Wrap (available from Kimberly-Clark) and processed through a STERRAD 1005 Low-Temperature Sterilizer for hydrogen peroxide sterilization (Standard cycle). After the hydrogen peroxide sterilization process was completed, the wrapped tray was removed from the sterilizer and placed on top of steam sterilized prepared sample strips of CE-1, EX-1 EX-2, and EX-3. Samples were allowed to contact with the residual hydrogen peroxide from the treated tray for approximately 20 hours. Subsequently, the optical density of the samples was recorded with the X-RITE 530 SpectroDensitometer, to assess the amount of color fading due to exposure to residual hydrogen peroxide emanating from the hydrogen peroxide sterilized load, Results are reported in Table 3.

TABLE 3

Results from the Hydrogen Peroxide Exposure Test

| Example | O.D. after steam sterilization | O.D. after 20 hr exposure to residual $H_2O_2$ fumes | % Color Retention |
|---|---|---|---|
| EX-1 | 1.66 | 1.58 | 94.74% |
| EX-2 | 1.74 | 1.66 | 95.68% |
| CE-1 | 1.62 | 1.24 | 76.79% |

Additional versions of the Examples were prepared with thicker ink and overcoat thicknesses. The "+" designation indicates the thicker ink and overcoat. Examples CE-1+, EX-2+, and EX-3+ were printed in strips on saturant treated crepe paper through a gravure printing process with a coating weight around 2 gsm. The resulting printed strips were then over-coated with a layer of an acrylic emulsion (25% solids HYCAR solution) with a coating weight of approximately 8 gsm (g/m$^2$). The finished samples were processed through a 4 minute exposure cycle in the same steam sterilizer as described above. The Hydrogen Peroxide Exposure Test was performed as described above. The % color retention measurement was recorded and is reported in Table 4.

Ink Transfer Test

Two layers of cotton towels were placed on top of a stainless steel instrument tray. Four paper pouches (PROPPER CHEX-ALL II Sterilization Pouches, available from Propper Manufacturing Company Inc. of Long Island City, N.Y.), each containing 2 replicated strip samples, were laid on top of the towels, but not on top of each other. Subsequently, an additional two layers of cotton towels were used to cover the samples placed in the paper pouches. Finally, a wrapped towel pack with 12 towels was placed on top of the prepped samples. The entire set up was then processed through the AMSCO Lab 110 sterilizer for a cycle exposure time of 6 minutes. After sterilization, the same procedure was applied to all samples until each sample was repeated in the same way. The inside surface of each pouch directly in contact with the printed indicator strips were scanned on a photocopier and analyzed through Image J software to quantify the migrated ink as a percentage. Image J software is a public domain, Java-based image processing program developed at the National Institutes of Health. Table 4 shows the results of the Ink Transfer Test.

TABLE 4

Results from the $H_2O_2$ fading test and ink transfer

| Sample | CE-1+ | EX-2+ | EX-3+ |
|---|---|---|---|
| O.D. after Steam | 1.58 | 1.31 | 1.20 |
| O.D. after 20 hour post $H_2O_2$ exposure | 0.61 | 0.71 | 0.69 |
| % O.D. Retention | 38.62% | 53.68% | 57.44% |
| % Ink Transfer | 3.13% | 0.00% | 0.02% |

Generally, a variety of known additives may be included in various formulations of the present disclosure. For example, surfactants and rheology modifiers can be added to suspend the insoluble components of the formulation as well as to improve print quality of the ink formulations. Dyes may be included to adjust the ultimate color achieved upon exposure to specific sterilization conditions. For example, in some embodiments, a dye may be included to shift the color from dark brown to black.

Various other modifications and alterations of this invention will become apparent to those skilled in the art without departing from the scope and spirit of this invention.

What is claimed is:

1. An indicator formulation comprising an indicating composition dispersed in water, wherein the indicating composition comprises
   (a) an organic Bi(III) compound;
   (b) a sulfur source;
   (c) a carbonate salt; and
   (d) strontium hydroxide;
   wherein at least one of the organic Bi(III) compound and the sulfur source has solubility in water at 20° C. of less than 5 grams/100 ml.

2. The indicator formulation of claim 1, further comprising water.

3. The indicator formulation of claim 1, wherein the indicating composition comprises bismuth subcarbonate formed in situ.

4. The indicator formulation according to claim 1, wherein both the organic Bi(III) compound and the sulfur source have solubility in water at 20° C. of less than 5 grams/100 ml.

5. The indicator formulation of claim 4, wherein at least one of the organic Bi(III) compound and the sulfur source have solubility in water at 20° C. of less than 1 gram/100 ml.

6. The indicator formulation according to claim 1, wherein the organic Bi(III) is selected from the group consisting of bismuth subsalicylate, bismuth citrate, bismuth tartrate, and combinations thereof.

7. The indicator formulation according to claim 1, wherein the sulfur source is selected from the group consisting of sulfur, 1,3-diphenylthiourea, sodium thiosulfate, and combinations thereof.

8. The indicator formulation according to claim 1, wherein the carbonate salt is selected from the group consisting of lithium carbonate, magnesium carbonate, sodium carbonate, sodium bicarbonate, and combinations thereof.

9. The indicator formulation according to claim 1, further comprising an acidic compound.

10. The indicator formulation of claim 9, wherein the acidic compound is non-polymeric.

11. The indicator formulation of claim 10, wherein the acidic compound is selected from the group consisting of citric acid, gallic acid, oxalic acid, and combinations thereof.

12. The indicator formulation according to claim 1, further comprising a resin.

13. The indicator formulation of claim 12, wherein the resin comprises an acrylic resin.

14. A method of preparing an indicator formulation comprising combining an organic Bi(III) compound; a sulfur source; a carbonate salt in water; and strontium hydroxide; wherein at least one of the organic Bi(III) compound and the sulfur source has solubility in water at 20° C. of less than 5 grams/100 ml, and reacting the organic Bi(III) compound with the carbonate salt to form bismuth subcarbonate.

* * * * *